(12) United States Patent
Moritz et al.

(10) Patent No.: US 9,126,199 B2
(45) Date of Patent: Sep. 8, 2015

(54) HANGING DROP PLATE

(75) Inventors: Wolfgang Moritz, Bassersdorf (CH);
Jens Kelm, Zürich (CH); Pierre-Alain Clavien, Kilchberg (CH); Simon Philip Hoerstrup, Zürich (CH)

(73) Assignee: Universitat Zurich Prorektorat Forschung, Zurich (CH)

( * ) Notice: Subject to any disclaimer, the term of this patent is extended or adjusted under 35 U.S.C. 154(b) by 391 days.

(21) Appl. No.: 13/120,215

(22) PCT Filed: Sep. 22, 2008

(86) PCT No.: PCT/CH2008/000391
§ 371 (c)(1),
(2), (4) Date: Aug. 29, 2011

(87) PCT Pub. No.: WO2010/031194
PCT Pub. Date: Mar. 25, 2010

(65) Prior Publication Data
US 2011/0306122 A1 Dec. 15, 2011

(51) Int. Cl.
*C12M 3/00* (2006.01)
*B01L 1/00* (2006.01)
*B01L 3/00* (2006.01)
*C12M 1/12* (2006.01)

(52) U.S. Cl.
CPC ............. *B01L 3/5085* (2013.01); *C12M 25/01* (2013.01); *B01L 2300/0829* (2013.01); *B01L 2300/0858* (2013.01)

(58) Field of Classification Search
CPC .......... B01L 2400/02; B01L 2400/022; B01L 2400/024; B01L 3/0241; B01L 3/0265; B01L 3/0268
See application file for complete search history.

(56) References Cited

U.S. PATENT DOCUMENTS

| 4,912,057 | A | * | 3/1990 | Guirguis et al. ............ 435/288.4 |
| 5,334,352 | A | * | 8/1994 | Johnson ......................... 422/500 |
| 5,882,930 | A | * | 3/1999 | Baier .............................. 436/49 |
| 7,399,448 | B2 | * | 7/2008 | Sundberg et al. ............. 422/503 |
| 2003/0235519 | A1 | | 12/2003 | Sha et al. |

(Continued)

FOREIGN PATENT DOCUMENTS

| KR | 100836827 | 6/2008 |
| WO | WO 03/078700 | 9/2003 |

(Continued)

OTHER PUBLICATIONS

International Search Report dated Aug. 12, 2009.

*Primary Examiner* — Nathan Bowers
(74) *Attorney, Agent, or Firm* — Cozen O'Connor

(57) ABSTRACT

A hanging drop plate and a method of cultivating cells or of producing molecular aggregates in at least one liquid volume that adheres to a drop contact area of such a hanging drop plate. The hanging drop plate has a body with a first surface and a second surface that is essentially coplanar to the first surface. The second surface has a drop contact area for adherently receiving a liquid volume. The drop contact area is distinguished from a surrounding area by a relief structure that prevents spreading of the liquid volume on the second surface of the body. The body has at least one conduit that mouths into the drop contact area from the direction of the first surface of the body. A liquid volume is applied to the drop contact area through a communicating conduit. Cells and/or molecules can be introduced into this liquid volume.

35 Claims, 5 Drawing Sheets

(56) References Cited

U.S. PATENT DOCUMENTS

2005/0118711 A1* 6/2005 Nordheim et al. ............ 435/366
2006/0281172 A1* 12/2006 Kuwabara et al. ......... 435/305.2
2007/0052781 A1* 3/2007 Fraden et al. .................. 347/96
2013/0084634 A1* 4/2013 Hsu et al. ...................... 435/325

FOREIGN PATENT DOCUMENTS

| | | |
|---|---|---|
| WO | WO 2005/089945 | 9/2005 |
| WO | WO 2008/123741 | 10/2008 |

* cited by examiner

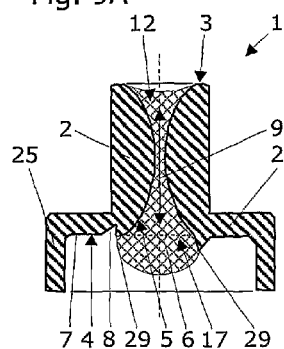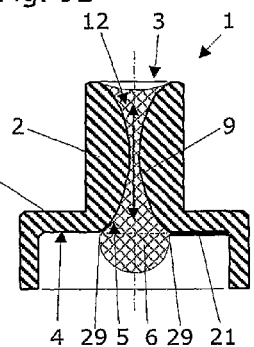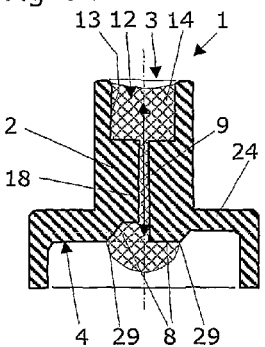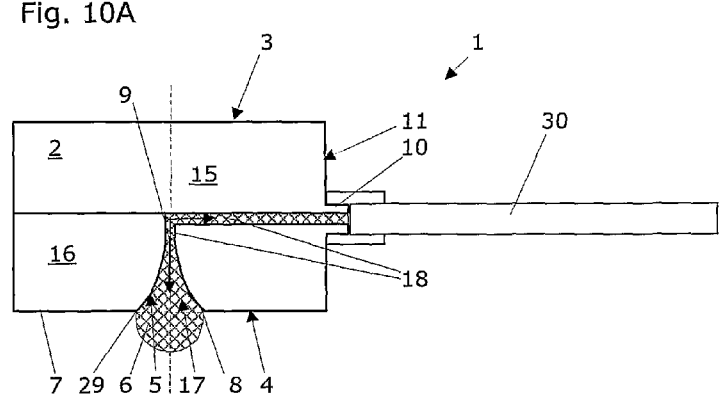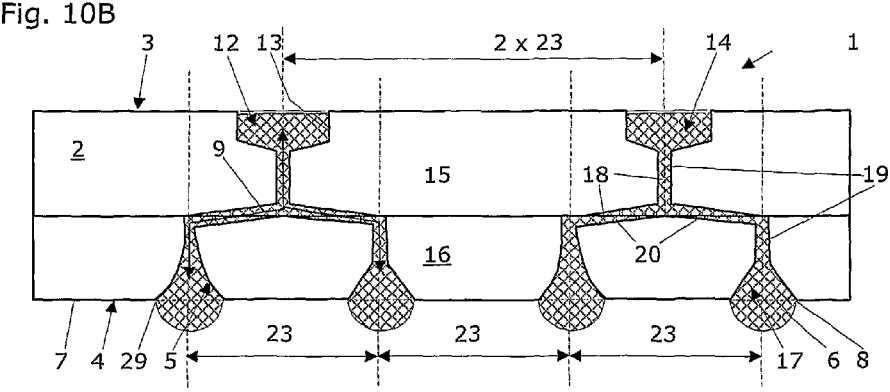

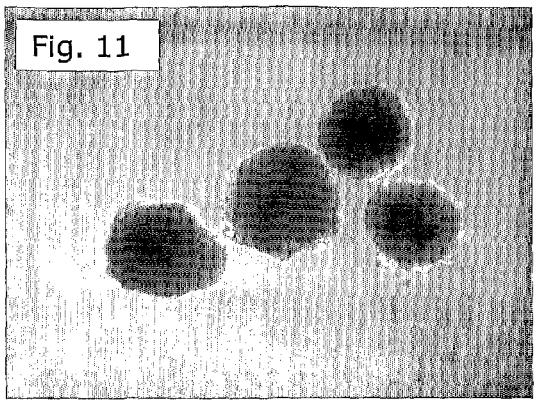
Fig. 11
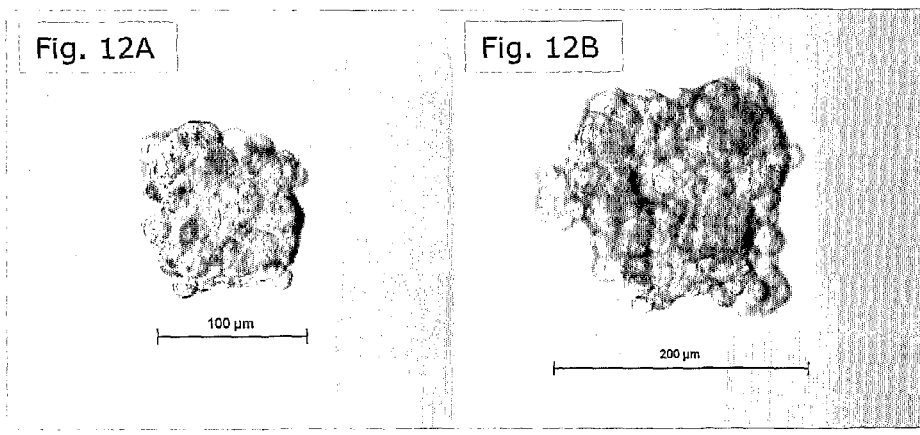
Fig. 12A
Fig. 12B
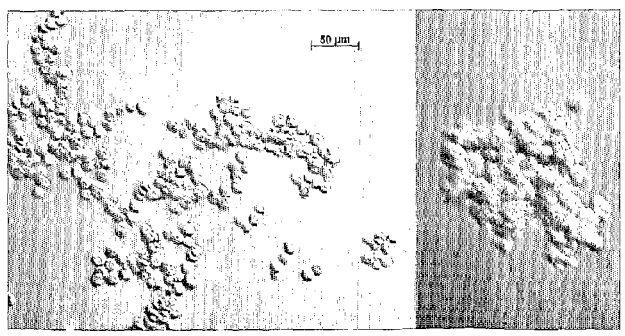
Fig. 13A
Fig. 13B
Fig. 13C

HANGING DROP PLATE

PRIORITY CLAIM

This is a U.S. national stage of application No. PCT/CH/2008/000391, filed on Sep. 22, 2008, the content of which is incorporated here by reference.

FIELD OF THE INVENTION

According to generic portion of the independent claim 1, the present invention relates to a hanging drop plate. This hanging drop plate comprises a body with a first surface and a second surface that is essentially coplanar to the first surface. The second surface comprises at least one drop contact area for adherently receiving a liquid volume. In this liquid volume, cells may be cultivated or molecular aggregates may be produced. This drop contact area is distinguished from a surrounding area by a relief structure that prevents spreading of the liquid volume on the second surface of the hanging drop plate body.

BACKGROUND OF THE INVENTION

It is generally accepted that cells cultured in a 3D configuration are physiological more relevant than cells in classical monolayer cultures (see e.g. Yamada and Cukiermann, Cell, 2007; Pamploni et al. Nature Reviews Molecular Cell Biology, 2007). Coaxing cells into the third dimension is the quintessential design problem. Current technologies are mostly based either on the use of scaffold materials or stacking of monolayers to shape the cells. However, despite the biological benefit, current state-of-the-art technologies are not laboratory routine or used on an industrial scale for applications such as drug discovery or toxicity assays given that the cell culture process is more complex, time-consuming and requires additional biomaterials. The re-aggregation of cells is an alternative approach to coax cells into the third dimension. But current re-aggregation technologies have been proven mostly with neoplastic cell lines and lack controlled co-culture possibilities. The hanging drop (HD-) technology has shown to be a universal method to enable 3D cell culture with neoplastic as well as primary cells (see Kelm and Fussenegger, 2004, Trends in Biotechnology Vol. 22, No. 4: 195-202). Drops of cell culture medium with suspended cells are placed onto a cell culture surface and the plate is inverted. As there is no substrate available on which the cells can adhere, they accumulate at the bottom of the drop and form a microtissue.

Cultivation of cells in drops that are hanging at a surface is well known to the person of skill in the art. Form DE 103 62 002 B4, for example, the usual way of depositing drops of a cell suspension in a nutrient medium with a pipette on the inner surface of a Petri dish cover is known. The Petri dish cover then has to be inverted and placed on an appropriate Petri dish base plate. In the so closed Petri dish, the drops hang from the cover surface. The Petri dish often contains wet filter paper for providing the hanging drops with a humid atmosphere that prevents the hanging drops from drying. One of the most critical steps of this conventional hanging drop technique is inverting the plate to which the drops are attached; thus, this crucial step very often has to be carried out manually by an experienced scientist.

From WO 03/078700 A1, the application of the hanging drop technique is known for culturing stem cells and for the production of protein crystals. The advantages of the hanging drop technology comprise the fact that the substances under investigation are completely surrounded with the nutrient medium that provides all factors needed, such as ions, differentiation factors, toxic substances etc. In addition, aggregation of cells (e.g. stem cells) is promoted in that the cells sink to the apex of the drop where they meet and form a cluster (e.g. embryonic bodies) without having touched a solid surface. The surface tension of the drop prevents the cells as well as the cell aggregates from penetrating the droplet surface. However, the drops applied with a pipette may comprise only a small volume as the drops may move on the surface during inverting the surface for providing the correct position to establish hanging drops. In order to provide larger drops of equal dimension and thus enabling identical cultivation or reaction environments, sharp-edged relief structures that limit a drop contact area on a particular surface are proposed.

More recently (see e.g. Kelm et al. 2004 or Khademhosseini et al. 2006, PNAS Vol. 103, No. 8: 2480-2487), cell culturing in hanging drops has been called microscale tissue engineering using gravity-enforced cell assembly. Whereby Khademhosseini et al. seem to favor microscale tissue engineering using template-based cell assembly in polyethylene glycol (PEG) microwells; Kelm and Fussenegger apply the hanging drop technique in wells of a multiwell or Terasaki plate.

All these documents report the necessity of inverting the substrate to which the drops adhere in order to correctly provide them as hanging drops. After being inverted, the substrates are reported to lay horizontal or to include an angle of at most 90° with the horizontal direction (see WO 03/078700 A1). Such inverting is difficult to handle manually and even more difficult to carry out by a robot. Thus, the required manual inversion of the plate impedes mass production and automation compatibility.

SUMMARY OF THE INVENTION

It is therefore an object of the present invention to provide a hanging drop plate that renders any unnecessary inverting of the substrate to which the drops adhere. Another object of the present invention is ability to perform medium exchange in a repetitive manner with minimal risk of aspirating and/or loosing microtissues.

These objects are achieved with a hanging drop plate which comprises a body with a first surface and a second surface that is essentially coplanar to the first surface and that comprises at least one drop contact area for adherently receiving a liquid volume for cultivating cells or for producing molecular aggregates therein, the at least one drop contact area being distinguished from a surrounding area by a relief structure that prevents spreading of the liquid volume on the second surface of the body, wherein the body further comprises at least one conduit that mouths into the at least one drop contact area from the direction of the first surface of the body. The hanging drop plate is characterized in that the body further comprises at least one conduit that mouths into the at least one drop contact area from the direction of the first surface of the body.

Advantages of the hanging drop plate and hanging drop technique according to the present invention comprise:
 there is no scaffold required;
 it is applicable to small liquid volumes and cell numbers;
 it provides size control of the cell aggregates;
 it is adaptable to a wide variety of cell/tissue types such as hepatic microtissues (e.g. HepG2), myocardial spheroids, and microcartilage;

it is capable to provide defined multi-cell type systems like for example an outer endothelial layer enveloping a core of fibroblasts;

the required cell aggregates can be produced in short production times;

a platform technology is provided that makes 3D cell culture technology as convenient as current 2D cell culture processes;

the system comprises a HD-plate format that fits a multi-well plate with e.g. 96 or 384 wells;

hanging drops are generated by top-loading using e.g. an automated multi-channel pipetting robot;

cell seeding and/or medium exchange can be carried out by an automated pipetter.

BRIEF DESCRIPTION OF THE DRAWINGS

The hanging drop plate of the present invention is now described in more detail on the basis of selected, exemplary embodiments that are depicted in schematic drawings, which shall illustrate preferred embodiments without delimiting the scope of the present invention. It is shown in:

FIG. 9 alternative variants of the first and second embodiment of the hanging drop plate, wherein FIG. 9A shows two alternative relief structures that prevent spreading of the liquid volume on the second surface of the body;

FIG. 9B shows two different surface treatments that prevent spreading of the liquid volume on the second surface of the body;

FIG. 9C shows two alternative relief structures that additionally provide minimizing or maximizing the drop volume;

FIG. 10 schematic cross sections of hanging drop plates that have a body, which comprises an upper part and a lower part that are attached to one another, wherein FIG. 10A shows a variant with a side inlet to fix a liquid line to the conduit;

FIG. 10B shows a variant with an open top inlet compartment that is fluidly connected to two or more conduits for supplying a 384 drop array with liquid dispensed from a 96 tip dispenser head;

FIG. 11 a microscopic image of neonatal rat cardiomyocytes as produced with a hanging drop plate according to FIG. 7;

FIG. 12 microscopic images of human hepatoma cells, wherein

FIG. 12A shows 100 cells/drop, and

FIG. 12B shows 250 cells/drop;

FIG. 13 microscopic images of rat pancreatic islet cells at different time points after seeding, wherein FIG. 13A shows the cells after 3 hours of incubation;

FIG. 13B shows the cells after 24 hours of incubation; and

FIG. 13C shows the microtissue after 96 hours of incubation.

DETAILED DESCRIPTION OF THE PRESENTLY PREFERRED EMBODIMENTS

Figure 1:
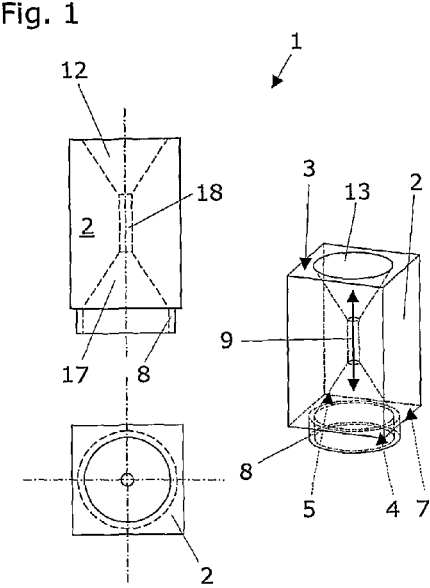
FIG. 1 a front and top view as well as a 3D representation of a unit cell of a hanging drop plate with a conduit that exhibits a cylindrical/frustoconical shape, according to a first embodiment.

FIG. 1 shows a front and top view as well as a 3D representation of a unit cell of a hanging drop plate with a conduit that exhibits a cylindrical/frustoconical shape (comprising a first truncated cone, a cylinder, and a second truncated cone), according to a first embodiment. The hanging drop plate 1 comprises a body 2 with a first surface 3 and a second surface 4 that is essentially coplanar to the first surface 3. The second surface 4 comprises at least one drop contact area 5 for adherently receiving a liquid volume 6 (see FIGS. 7 and 8) for cultivating cells or for producing molecular aggregates therein. The at least one drop contact area 5 is distinguished from a surrounding area 7 by a relief structure 8 that prevents spreading of the liquid volume 6 on the second surface 4 of the body 2. The body 2 further comprises at least one conduit 9 that mouths into the at least one drop contact area 5 from the direction of the first surface 3 of the body 2.

The relief structure 8 in this case is accomplished as a circular rim and the conduit 9 penetrates the entire body 2 in an essentially perpendicular direction from the first surface 3 to the second surface 4. The conduit 9 comprises an inlet compartment 12 that is situated close to the first surface 3 of the body 2. Here, the inlet compartment 12 is accomplished as a widened portion 13 of the conduit 9 inside of the body 2, which is accomplished as one integral element. The conduit 9 comprises a culture compartment 17 that is situated close to the second surface 3 of the body 2 and that comprises at least a part of the drop contact area 5. In this embodiment, the culture compartment 17 is accomplished as a funnel-shaped depression with straight walls. The conduit 9 comprises a capillary portion 18 with a diameter of at least 10 µm, preferably between 10 µm and 500 µm, most preferably between 50 µm and 200 µm. The cylindrical capillary portion 18 of the conduit 9 has a length between 0.1 mm and 30 mm, preferably between 0.5 mm and 2 mm. As can be seen from the FIG. 1, the conduit 9 is accomplished as an un-branched channel that essentially extends perpendicularly to the first and second surfaces 3,4 and all portions of the conduit 9 are coaxially aligned.

Figure 2:
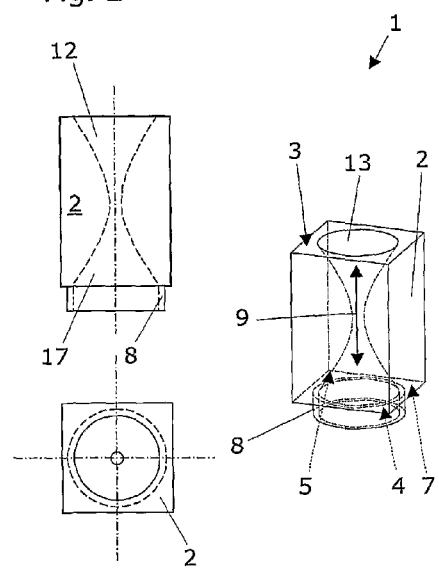
FIG. 2 a front and top view as well as a 3D representation a unit cell of a hanging drop plate with a conduit that exhibits a hyperboloid shape, according to a second embodiment.

FIG. 2 shows a front and top view as well as a 3D representation of a unit cell of a hanging drop plate with a conduit that exhibits a hyperboloid shape, according to a second embodiment. Most of what has been said about the first embodiment also applies here. In this embodiment however, the culture compartment 17 is accomplished as a funnel-shaped depression with curved walls. The conduit 9 comprises a capillary portion 18 with a diameter of at least 10 µm, preferably between 10 µm and 500 µm, most preferably between 50 µm and 200 µm. The cylindrical capillary portion 18 of the conduit 9 has a length of 0 mm here and the conduit 9 again is accomplished as an un-branched channel that essentially extends perpendicularly to the first and second surfaces 3,4, and all portions of the conduit 9 being coaxially aligned. Deviating from the presentation in FIG. 2, the length of the cylindrical capillary portion 18 of the conduit 9 could be up to 30 mm as well.

Figure 3:
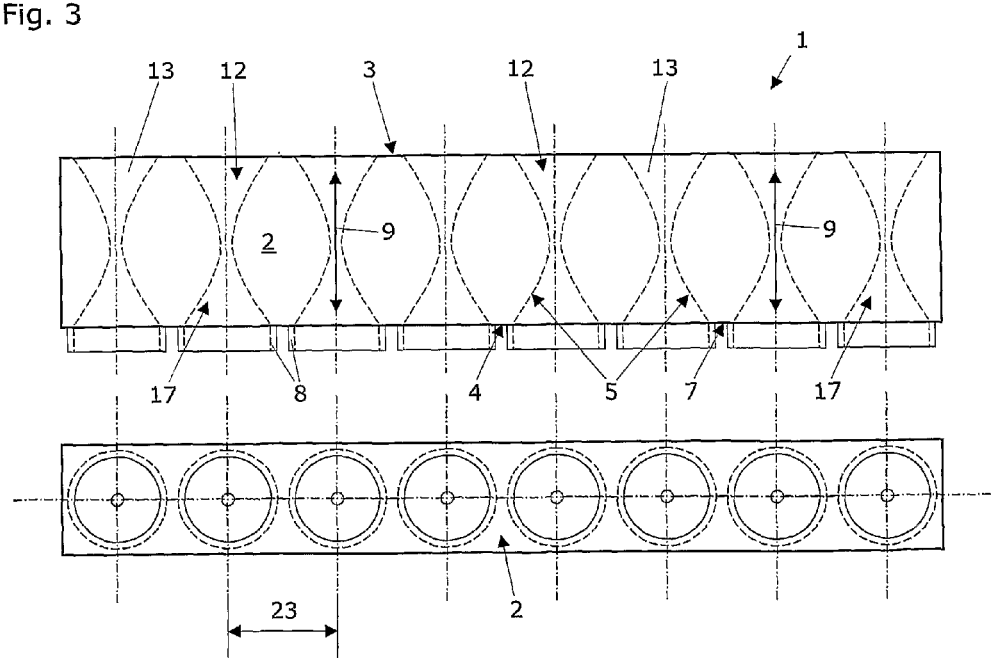
FIG. 3 a front and top view of a linear array of unit cells of a hanging drop plate with a conduit that exhibits a hyperboloid shape, according to the second embodiment.

FIG. 3 shows a front and top view of a linear array of unit cells of a hanging drop plate with a conduit that exhibits a hyperboloid shape, according to the second embodiment (see FIG. 2). The axes of the unit cells are spaced by a repetitive axial distance 23, which preferably is 18 mm, 9 mm, or 4.5 mm according to the axial distances of well known standard microplates with 24, 96, or 384 wells (see the published standard dimensions of microplates American National Standards Institute/Society for Biomolecular Sciences: ANSI/SBS 1-2004, ANSI/SBS 2-2004, ANSI/SBS 3-2004, ANSI/SBS 4-2004).

Figure 4:
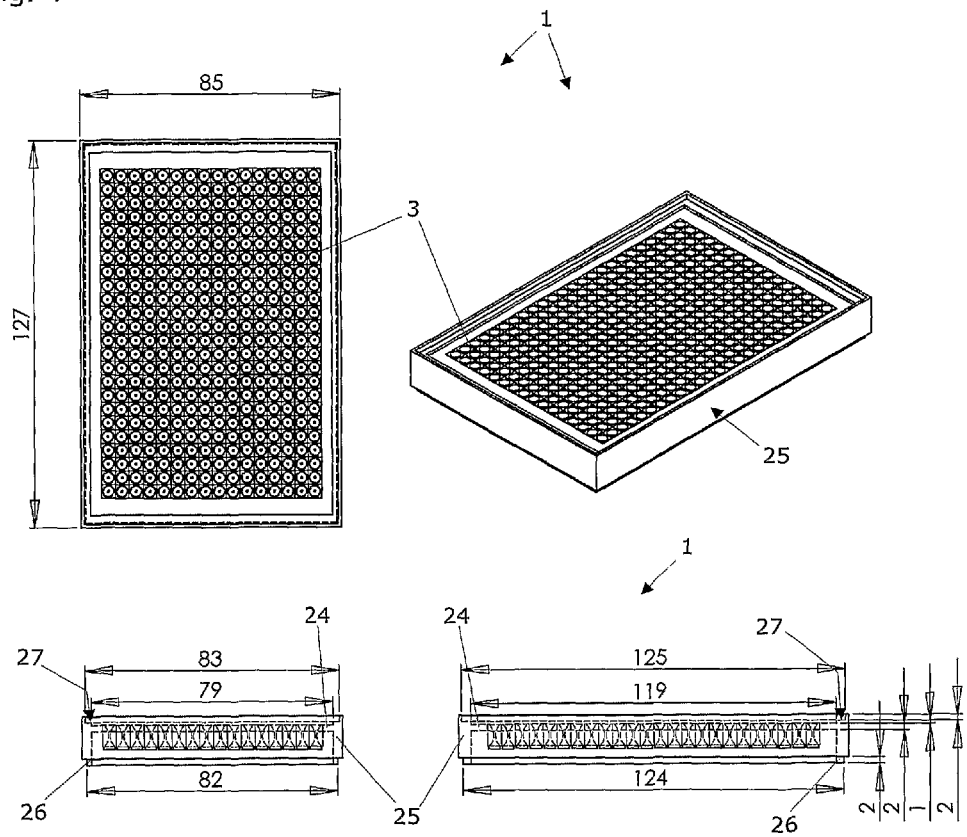
FIG. 4 a front, a side and a top view as well as a 3D representation of a two dimensional array of unit cells of a hanging drop plate with a conduit that exhibits a hyperboloid shape, according to the second embodiment.

FIG. 4 shows two front views and a top view as well as a 3D representation of a two dimensional array of unit cells of a hanging drop plate with a conduit that exhibits a hyperboloid shape, according to the second embodiment. Preferred dimensions are indicated and are very close to the dimensions of a standard microplate. Actually, a two dimensional array of 384 drop contact areas 5 and conduits 9 is depicted here. The axial distances thus preferably are 4.5 mm in order to meet the ANSI/SBS standard and to be able to incorporate the array of 384 drop contact areas 5 and conduits 9 in a hanging drop plate 1 with the dimensions that are at least approximately the dimensions of a standard microplate. Whereas the unit cells of the hanging drop plate 1 preferably are in close contact to each other (like also depicted in FIG. 3), the array of these unit cells preferably is surrounded by a horizontal plate 24. The horizontal plate 24 itself preferably is surrounded by a vertical rim 25 that exhibits a lower web 26 and an upper depression 27. The web 26 and the depression 27 are of such dimensions that they serve as stacking means for tightly stacking the hanging drop plates 1 and for safely holding the stacked plates in place. As can be seen from the FIG. 4, the height of the web 26 and the depression 27 preferably is about 2 mm in each case.

Departing from the presentation of FIG. 4, the position of the web 26 and the depression 27 could be interchanged without losing their function as stacking means. Also the dimensions of the horizontal plate 24 and the vertical rim 25 could be changed without departing from the spirit of the present invention. However, it is preferred in any case that the vertical rim 25 protrudes over the first surface 3 and below the second surface 4 of the hanging drop plate 1. It is especially preferred (see FIG. 4) that the vertical rim 25 also protrudes below the relief structure 8 on the second surface 4 of the hanging drop plate 1. Such a protruding vertical rim 25 additionally secures the first and second surfaces 3,4 of the hanging drop plate 1 from being damaged or touched. Also the danger of contamination of these two surfaces is greatly reduced by the vertical rim 25.

Figure 5:
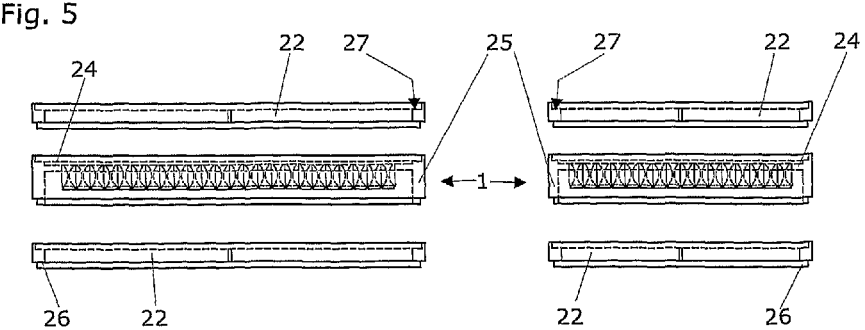
FIG. 5 a front and a side view of a two dimensional array of unit cells of a hanging drop plate with a conduit that exhibits a hyperboloid shape, according to the second embodiment in combination with a top and bottom cover plate.

FIG. 5 shows a front and a side view of a two dimensional array of unit cells of a hanging drop plate with a conduit that exhibits a hyperboloid shape, according to the second embodiment in combination with a top and bottom cover plate. As in FIG. 4, a two dimensional array of 384 drop contact areas 5 and conduits 9 is depicted here. Again, the array of these unit cells preferably is surrounded by a horizontal plate 24, which preferably is surrounded by a vertical rim 25 that exhibits a lower web 26 and an upper depression 27. The web 26 and the depression 27 are of such dimensions that they serve as stacking means for tightly stacking the hanging drop plates 1 and for safely holding the stacked plates in place. It is especially preferred that the cover plate 22 also exhibits a lower web 26 and an upper depression 27 that correspond with those of the hanging drop plate 1. Of particular preference is a cover plate 22 that is accomplished to be used as a bottom and/or top cover plate as the case may be. This has the advantage that the same cover plate 22 can be used as shell underneath the hanging drop plate 1 or as a cap on top of it.

Especially during cultivation or incubation in the process of cultivating cells or of producing molecular aggregates in at least one liquid volume 6 that adheres to a drop contact area 5 of a hanging drop plate 1, it is preferred to cover the hanging drop plate 1 on the top and bottom side in order to avoid unacceptable evaporation of the liquid in the liquid volume 6 or in the conduit 9. Preferably at the bottom of a first hanging drop plate 1, a cover plate 22 is placed as a bottom shell plate. This first hanging drop plate 1 can be covered by a second cover plate 22 that is now used as a cap. Such a "sandwich" of two cover plates 22 and one hanging drop plate 1 between them is the smallest unit preferably formed for storage, cultivation or incubation, and safe transport of a hanging drop plate, whether it is loaded with liquid volumes and cells and/or molecules or not (see FIG. 5).

For incubation or cultivation in device with a temperature control, several hanging drop plates 1 can directly be stacked on top of each other and only covered on the top and the bottom of the uppermost and lowermost hanging drop plate 1 with a cover plate 22. This is especially preferred when all hanging drop plates of a stack are loaded with the same samples so that no cross contamination is to be feared at all. If however different samples are loaded (within the same or different hanging drop plates 1 of a stack), it is preferred to separate the hanging drop plates 1 with an intermediately placed cover plate 22 between each of the hanging drop plates 1.

Figure 6:
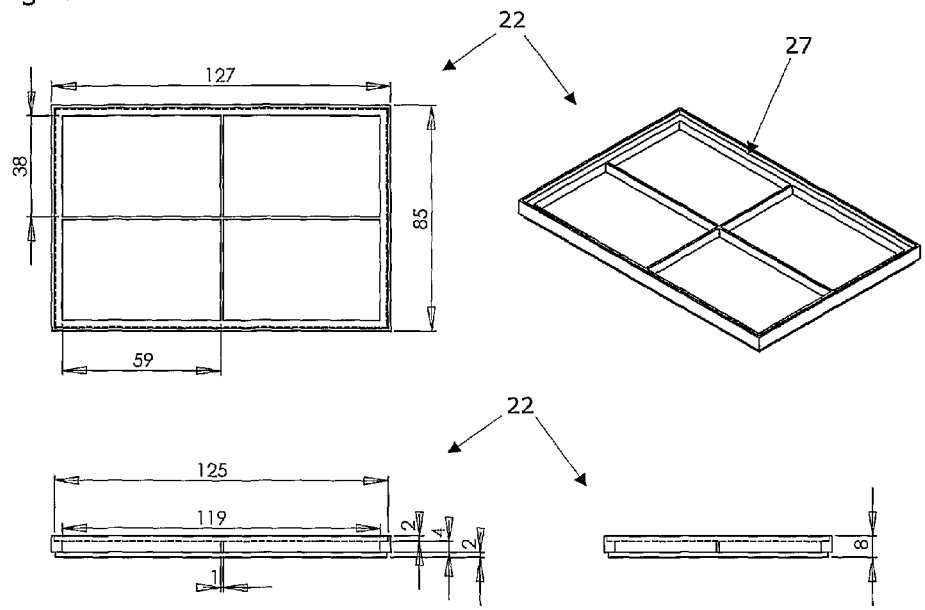
FIG. 6 a front, a side and a top view as well as a 3D representation of the cover plate of FIG. 5.

Of course it is possible to produce individual hanging drop plates 1 (see FIG. 4) and separate cover plates 22 (see FIG. 6); it is just preferred to have the same dimensions of the lower web 26 and an upper depression 27 in each case. However, the most preferred set for cultivating cells or for producing molecular aggregates preferably comprises one hanging drop plate 1 and two cover plates 22.

Figure 7:
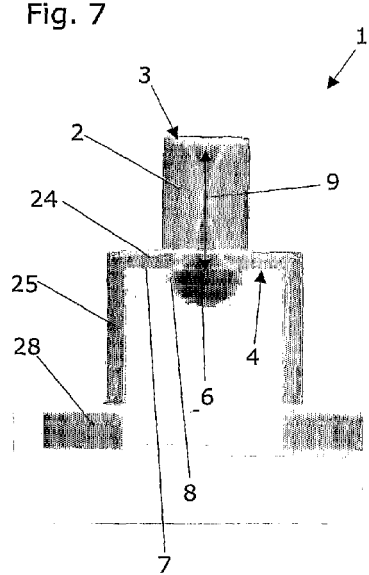
FIG. 7 a photographic image of a culture medium drop, hanging at the drop contact area of the hanging drop plate with a conduit that exhibits a hyperboloid shape, according to the second embodiment; the conduit being essentially filled with culture medium.

FIG. 7 shows a photographic image of a culture medium drop, hanging at the drop contact area 5 of the hanging drop plate 1 with a conduit 9 that exhibits a hyperboloid shape, according to the second embodiment. It is evident that the conduit 9 essentially is filled with culture medium. This holding the drop (i.e. the liquid volume 6) at the drop contact area 5 is due to a combined action of different elements:

a) The capillary force of the conduit 9 is working against the gravity and the hydrostatic force in the conduit 9 and the liquid volume 6 that attract the drop.
b) An eventually present selective hydrophilic coating in the drop contact area 5 supports the adhesion of the liquid volume 6 and works against the hydrostatic force and the gravity.
c) The relief structure 8 (accomplished as a rim here) stabilizes the liquid volume 6 and supports the definition of the actual content of the liquid volume.
d) The surface tension of the drop additionally stabilizes the liquid volume 6.
e) A selective hydrophobic coating 21 applied to the surrounding area 7 of the hanging drop plate 1 additionally may stabilize the liquid volume 6.

Actually, the image has been taken from a prototype of a linear array of unit cells of a hanging drop plate 1 with a conduit 9 that exhibits a hyperboloid shape, according to a second embodiment (see FIGS. 2 and 3). In order to place the prototype in a Petri dish that was used as a bottom shell, the prototype had been equipped with a horizontal plate 24, a vertical rim 25, and a stand plate 28 that all surround the unit cells of the hanging drop plate 1. Thus, between the unit cells, the horizontal plate 24 and the vertical rim 25 of the prototype hanging drop plate 1 and the Petri dish below (not visible here), a practically closed space was formed, which allowed a saturated humid atmosphere to be kept around the liquid volumes 6 situated at the respective drop contact areas 5.

Figure 8:
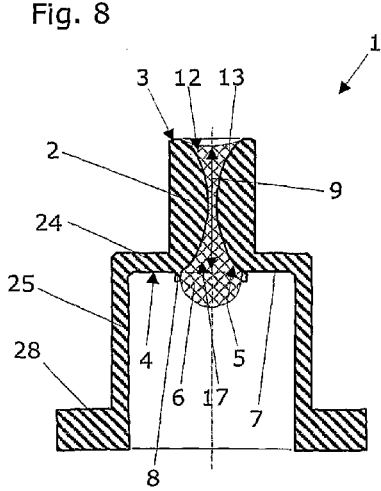
FIG. 8 a schematic cross section of the photographic image in FIG. 7.

To support understanding the image, the FIG. 8 shows a schematic cross section of the photographic image in FIG. 7. As in all Figures, the same reference numbers direct to the same or similar features, even if they are not discussed in detail in each case.

FIG. 9 shows alternative variants of the first and second embodiment of the hanging drop plate. The layout of the hanging drop plate 1 is according to the prototype shown in the FIGS. 7 and 8. However, also single unit cells or entire hanging drop plates 1 with the approximate shape and dimension of a standard microplate could also show unit cells according to the variants shown here.

FIG. 9A shows two alternative relief structures 8 that prevent spreading of the liquid volume 6 on the second surface 4 of the body 2 of the hanging drop plate 1 according to the invention. The relief structure 8 (instead of being a rim) may be accomplished as ring-like depression (see left side) or as ring-like elevation (see right side). In any case, an abrupt change of direction in the profile of the relief structure 8 is safely defining the border of the liquid volume 6 or the drop.

FIG. 9B shows two different surface treatments that prevent spreading of the liquid volume 6 on the second surface 4 of the body 2 of the hanging drop plate 1 according to the invention. On the left side, the drop contact area 5 is selectively coated with biologically active compounds, which are selected from a group comprising polypeptides (antibodies, growth factors, enzymes) and polynucleotides (RNA, DNA single or double strands). On the right side the surrounding area 7 is selectively coated with a hydrophobic coating 21. A combination of these two treatments is especially preferred as well. The utilization of a hydrophobic coating 21 may even dispense with the necessity to incorporate a relief structure in the form of an additional rim or depression at the second surface 4. Thus, the edge 29 shown here is sufficient as a relief structure 8.

FIG. 9C shows two alternative relief structures that additionally provide minimizing or maximizing the drop volume. On the left side, a depression with an edge 29 is formed. Here, the drop volume is maximized. On the right side, an elevation with an edge 29 is formed; thus, minimizing the drop volume. In addition, a hanging drop plate 1 is shown here, the conduit 9 of which comprises an inlet compartment 12 that is situated close to the first surface 3 of the body 2. Preferably, the inlet compartment 12 is accomplished as a widened portion 13 of the conduit 9 inside of the body 2 (see e.g. FIGS. 9A and 9B) or as a cup 14 on the first surface 3 of the body 2 as depicted here. A combination of such a widened portion 13 and a cup 14 is also feasible (not shown).

It is important to note here that any combination of the features shown in the Figures and/or described in the specification can be utilized and is comprised by the spirit of the present invention.

FIG. 10 shows schematic cross sections of hanging drop plates 1 that have a body 2, which comprises an upper part 15 and a lower part 16 that are attached to one another. This two-part arrangement greatly facilitates the production of an alternative hanging drop plate 1 with a conduit 9 that partly penetrates the body 2 in an essentially perpendicular direction in the region of the at least one drop contact area 5 and that partly extends essentially parallel to the second surface 4 of the hanging drop plate 1.

FIG. 10A shows a variant with a side inlet to fix a liquid line to the conduit. Here, the conduit 9 comprises an inlet connection 10 that is situated at a side front 11 of the body 2. Different to the embodiments shown in the FIGS. 1 to 8, where the liquids preferably are delivered to the conduits 9 of the hanging drop plate 1 with one or more pipettes or with a pipetting robot, lines 30 can directly be connected to a hanging drop plate 1. Through such lines 30, liquids as well as cells or molecules can be delivered at any time to the liquid volumes 6 of a hanging drop plate 1. Thus, exchange of liquids, such as buffers or washing liquids in the liquid volumes 6 is facilitated.

FIG. 10B shows a variant with an open top inlet compartment that is fluidly connected to two or more conduits for supplying a 384 drop array with liquid dispensed from a 96 tip dispenser head. Here, the conduit 9 in addition penetrates the first surface 3 of the body 2 in an essentially perpendicular direction and the conduit 9 is accomplished as a branched channel comprising channel parts 19 that essentially extend perpendicularly to the first and second surfaces 3,4 and branch parts 20 that essentially extend parallel to the second surface 4. Whereas the drop contact areas 5 can be spaced apart by an axial distance 23 of 4.5 mm, the open top inlet compartments 12 then preferably are spaced apart by 9 mm or the double axial distance 23. In a linear array hanging drop plate 1 (compare to FIG. 3), two branch parts 20 join a common channel part 19. In a 2D-array hanging drop plate 1 (compare to FIG. 4), four branch parts 20 join a common channel part 19. Thus, with a robot that comprises a 96 tip dispenser head a hanging drop plate 1 with a 384 drop array can be supplied with liquid and/or cells or molecules at once.

Complementary control of the drop shape and position can be obtained by selective coating of the inside surface of the culture compartment 17, the ridge 8 and the surrounding plate 7 to achieve hydrophilic and hydrophobic areas. Also, the inside surfaces of both compartments 12,17 and the conduit 9 can be coated with a surface film that prevents cells from adhering to the surface. Alternatively the surface can be patterned directly using micro- and nano-machining techniques to prevent adhesion.

The hanging drop plates 1 are preferably tissue culture plates of standard outer dimensions (ANSI/SBS 1-2004) compatible with high throughput systems. As shown, the hanging drop plate 1 set preferably consists of two elements:
a) a hanging drop plate 1 containing the hanging drop wells or drop contact areas 5; and
b) a cover 22 supporting the hanging drop plate 1.

Both elements (hanging drop plate 1 and cover 22) are made out of or at least comprise at their respective surfaces a biocompatible plastic material (e.g. Polycarbonate, Polyethylene, Polystyrene, or Polypropylene). Both elements (hanging drop plate 1, cover 22) are compatible with photometric readers (reading from the top and bottom, preferably bottom reading). The hanging drop plate 1 contains preferably 96 or 384 units of the hanging drop wells. The hanging drop plate 1 preferably is equipped with a vertical rim 25 for cover-independent robotic handling. The cover 22 provides enough space for drop formation within each single unit of the hanging drop plate 1. Hanging drop plates 1 are designed to be stacked onto each other. Covers 22 can be equipped with a narrow channel system or trough along the inner side of the base allowing to be filled with water/saline in order to minimize drop evaporation. Covers 22 can be used for both, lower and upper shells of hanging drop plates 1 to minimize evaporation and protect from contaminations.

Hanging drops can be generated by top loading of liquids into the inlet compartment 12 by standard single channel or multichannel pipettes, in a manual or automated fashion. The design of the hanging drop well allows repeated liquid exchange through the inlet compartment 12.

The present invention provides a device for coaxing and culturing of cells into the third dimension without artificial substrate-cell interactions. The device comprises a microfluidic system with two compartments (inlet compartment 12 and culture compartment 17). The volume of the inlet compartment 12 is preferably between 5 µl and 50 µl, most preferably between 10 µl, and 30 µl. The volume of the culture compartment 17 is preferably between 10 µl and 100 µl, most preferably between 10 µl and 50 µl. The shapes of inlet compartment 12 and culture compartment 17 can be cylindrical, conical or hyperbolical. Each culture volume of a single unit preferably connects to a ring 8 which protrudes from the culture compartment bottom to stabilize and separate individual drops. The height of the drop separator ring or relief structure 8 in the form of a ridge is preferably between 0.1 mm and 5 mm, most preferably between 1 and 2 mm.

The hanging drop plate 1 according to the invention can be made directly by injection molding or laterally by replica molding. Alternative production methods comprise micromilling techniques and/or gluing or welding parts of the hanging drop plate 1 together.

In the following, the materials and methods as well as the achieved results when using the prototype of the hanging drop plate 1 according to the present invention shall be briefly described.

A typical protocol for the production of a hanging drop culture is as follows:
a) Harvest cells from conventional 2D-culture by standard trypsinization.
b) Wash cells with regular cell culture medium.
c) Take up cells in an appropriate volume of regular cell culture medium with a density of 3'333 to 333'333 cells/ml corresponding to 100 to 10'000 cells/30 µl drop or liquid volume 6 respectively depending on experimental requirements.
d) Gently swirl the flask containing the cells and dispense drops of 30 µl of cell suspension into the inlet compartments 12 of the hanging drop plate 1 by top loading.
e) Place the hanging drop plate 1 into a humidified box in a regular cell culture incubator.
f) Cells will aggregate and form microtissues within 1-3 days, depending on the type of cells.
g) Long term incubations or experimental protocols will eventually require a change of medium. This is performed by simply aspirating up to 25 µl of old medium from the inlet compartments 12 on the top side of the hanging drop plate 1 and by replacing by a similar volume of fresh medium that is pipetted into the inlet compartments 12.
h) Harvest microtissues by rinsing the drop contact areas 5 with 50 to 100 µl of medium delivered to the inlet compartments 12 on the top side of the hanging drop plate 1 and by thus rinsing the microtissues into a collection device (i.e. a Petri dish or a microplate with 96 or 384 wells).

EXAMPLE I

Freshly isolated cardiomyocytes from neonatal rats were produced according to the above protocol not including cell harvesting from 2D cultures (point a from the protocol). The resulting microtissues produced from 10'000 cells/drop correspond to a microtissue size of about 250 µm in diameter. This is demonstrated in FIG. 11 that shows a microscopic image of rat cardiomyoyte-composed micro-tissues produced with a hanging drop plate according to FIG. 7.

EXAMPLE II

Human hepatoma cells (HepG2) were treated according to the above protocol. FIG. 12 shows microscopic images of human hepatoma microtissues 48 hours after seeding with 100 cells per drop (FIG. 12A) and 250 cells per drop (FIG. 12B). These cell densities resulted in microtissues of 100 µm and 200 µm in diameter respectively.

EXAMPLE III

Rat pancreatic islet cells (250 cells per drop) were treated according to the above protocol as it is demonstrated in the FIG. 13 that shows microscopic images of rat pancreatic islet cells at different time points after seeding. The formation of the rat pancreatic islet microtissue can be followed: After 3 hours of incubation, practically only single cells are present (see FIG. 13A). After 24 hours of incubation, practically all cells have aggregated (see FIG. 13B). After 96 hours of incubation, a spherical rat pancreatic islet microtissue with a diameter of approximately 100 µm has been formed (see FIG. 13C).

Thus, the present invention comprises a method of cultivating cells or of producing molecular aggregates in at least one liquid volume 6 that adheres to a drop contact area 5 of a hanging drop plate 1 as described on the base of the FIGS. 1 to 10. The hanging drop plate 1 comprises a body 2 with a first surface 3 and a second surface 4 that is essentially coplanar to the first surface 3 and that comprises at least one drop contact area 5 for adherently receiving the at least one liquid volume 6 therein. The at least one drop contact area 5 is distinguished from a surrounding area 7 by a relief structure 8 that prevents spreading of the liquid volume 6 on the second surface 4 of the body 2. The method according to the present invention is characterized in that a liquid volume 6 is applied to a drop contact area 5 through a conduit 9 that mouths into the drop contact area 5 from the direction of the first surface 3 of the body 2.

When carrying out the method of cultivating cells, preferably, a number of cells or cellular micro-aggregates of at least one cell type are
 suspended in a liquid,
 moved trough a conduit 9 of the hanging drop plate 1 together with a liquid volume 6,
 cultivated within the liquid volume 6; and
a microtissue is formed within the liquid volume 6 from the cultivated cells.

Alternatively when carrying out the method of cultivating cells, a number of cells or cellular micro-aggregates of at least one cell type are
 moved trough a conduit 9 of the hanging drop plate 1 into a liquid volume 6,
 cultivated within the liquid volume 6; and
a microtissue is formed within the liquid volume (6) from the cultivated cells.

When carrying out the method of producing molecular aggregates, preferably, a number of molecules or molecular micro-aggregates are
 suspended in a liquid,
 moved trough a conduit 9 of the hanging drop plate 1 together with a liquid volume 6,
 incubated within the liquid volume 6; and a molecular aggregate is formed within the liquid volume 6 from the incubated molecules or molecular micro-aggregates.

Preferably when carrying out the method of cultivating cells or of producing molecular aggregates, a part of the liquid in the liquid volume 6 is withdrawn through the respective conduit 9 of the hanging drop plate 1 that is dedicated to the drop contact area 5. In the following, it is preferred to replace at least a part of the withdrawn liquid by a liquid that is delivered through the respective conduit 9 of the hanging drop plate 1 that is dedicated to the drop contact area 5.

Of particular interest is the use of the of the hanging drop plate 1 according to the invention in:

a) Drug screening and development: The hanging drop plate provides a platform for manual (low volume) or automated (high volume) generation of biomimetic 3D cellular aggregates, i.e. microtissues, with improved tissue specific function. Full compatibility to robotic liquid handlings systems will enable high throughput compound screening for lead identification and lead optimization subsequent to the re-aggregation process without the requirement of further cell passaging. Microtissue based assays can be performed in a regular manner as with conventional 2D cell based assays with end-point determination by either microscopic, photometric, fluorometric, and/or luminometric measurements (bottom reading) and/or further downstream tissue processing (histological analysis).

b) Cell-based toxicity testing (ADME/tox): The hanging drop plate provides a platform for manual or automated generation of 3D cellular aggregates, i.e. microtissues, with improved tissue specific function. Full compatibility to robotic liquid handlings systems will enable high throughput testing of potential drug candidates involving the aspects of adsorption, metabolism, excretion and toxicology. Microtissue based assays can be performed in a regular manner as with conventional 2D cell based assays with end-point determination by either microscopic, photometric, fluorometric, and/or luminometric measurements (bottom reading) and/or further downstream tissue processing (histological analysis).

c) Cell-based therapy: Microtissues display several advantages for cell-based therapies compared to single cell treatment comprising (i) higher functionality, (ii) preformed extracellular matrix, (iii) secretion of proangiogenic factors such as vascular endothelial growth factor and lower motility as single cells. Therefore microtissues have a higher potential for tissue regeneration/repair to treat various organic disorders such as myocardial infarct or diabetes. Mass production is an indispensable prerequisite for their use in cell based therapies. The hanging drop plate provides mass production compatibility by following features as outline previously:
1. requires low culture volume
2. simultaneous top loading or withdrawal by dispenser with up to 384-channels
3. inlet compartment fluidly connected to two or more conduits, serving two or more drops per dispenser channel
4. stackability of hanging drop plates The hanging drop plate further facilitates the application of complex procedures such as expansion and subsequent time dependent differentiation protocols, involving repetitive media changes for the conversion of omni- or pluripotent precursor cells into highly differentiated cell aggregates with tissue specific functionality.

d) Protein crystallization: To investigate protein function, understanding the 3-dimensional structure is mandatory. Protein crystals are generated by slowly increasing the protein concentration in hanging drops of specific liquids by evaporation processes. The hanging drop plate enables robotic compatible seeding, raising and harvesting of protein/molecular crystals.

REFERENCE NUMBERS

1 hanging drop plate
2 body
3 first surface
4 second surface
5 drop contact area
6 liquid volume
7 surrounding area
8 relief structure
9 conduit
10 inlet connection
11 side front of 2
12 inlet compartment
13 widened portion
14 cup
15 upper part of 2
16 lower part of 2
17 culture compartment
18 capillary portion
19 channel parts
20 branch parts
21 hydrophobic coating
22 cover plate
23 axial distance
24 horizontal plate
25 vertical rim
26 lower web
27 upper depression
28 stand plate
29 edge
30 line

The invention claimed is:
1. A set for cultivating cells or for producing molecular aggregates, the set comprising a hanging drop plate; wherein the hanging drop plate comprises a body with a first surface and a second surface that is essentially coplanar to the first surface and that comprises at least one drop contact area for adherently receiving a liquid volume for cultivating cells or for producing molecular aggregates therein, the at least one drop contact area being distinguished from a surrounding area by a relief structure that prevents spreading of the liquid volume on the second surface of the body, wherein the body further comprises at least one conduit that leads into the at least one drop contact area from the direction of the first surface of the body, the conduit comprising a culture compartment that is situated close to the second surface of the body and that comprises at least a part of the drop contact area,
wherein the culture compartment comprises a widened portion of the conduit, and
wherein the culture compartment has a shape consisting of a truncated cone,
the conduit comprises the culture compartment, a second truncated cone oriented such that a larger diameter opening of the second truncated cone is proximate the first surface of the body, and a capillary portion in commu- nication with a smaller diameter opening of the truncated cone and a smaller diameter opening of the second truncated cone.

2. The set according to claim 1, wherein the hanging drop plate comprises a relief structure selected from a group that comprises a rim, a bulge, a depression, an elevation, and any combination thereof and is located in or on the second surface.

3. The set according to claim 1, wherein the conduit penetrates the entire body in an essentially perpendicular direction from the first surface to the second surface.

4. The set according to claim 1, wherein the conduit partly penetrates the body in an essentially perpendicular direction in the region of the at least one drop contact area and partly extends essentially parallel to the second surface.

5. The set according to claim 4, wherein the conduit comprises an inlet connection that is situated at a side front of the body.

6. The set according to claim 4, wherein the conduit in addition penetrates the first surface of the body in an essentially perpendicular direction.

7. The set according to claim 1, wherein the conduit comprises an inlet compartment that is situated close to the first surface of the body.

8. The set according to claim 4, wherein the body comprises an upper part and a lower part that are attached to one another.

9. The set according to claim 1, wherein the conduit comprises a capillary portion with a diameter of at least 10 μm.

10. The set according to claim 1, wherein the conduit comprises an un-branched channel that essentially extends perpendicularly to the first and second surfaces, wherein all portions of the conduit are coaxially aligned.

11. The set according to claim 1, wherein the conduit comprises a branched channel comprising channel parts that essentially extend perpendicular to the first and second surfaces and branch parts that essentially extend parallel to the second surface.

12. The set according to claim 1, having at least essentially the shape of a standard micro plate and wherein the drop contact areas are arranged in an array of 4×6, 8×12, or 16×24 drop contact areas.

13. The set according to claim 1, wherein the capillary portion is cylindrical.

14. The set according to claim 1, further comprising two cover plates, one of the cover plates configured for use as a bottom plate of the hanging drop plate and the other of the cover plates configured for use as a top plate for the hanging drop plate.

15. The set according to claim 13, wherein the cylindrical capillary portion of the conduit has a length between 0.1 mm and 30 mm.

16. A set for cultivating cells or for producing molecular aggregates, the set comprising a hanging drop plate; wherein the hanging drop plate comprises a body with a first surface and a second surface that is essentially coplanar to the first surface and that comprises at least one drop contact area for adherently receiving a liquid volume for cultivating cells or for producing molecular aggregates therein, the at least one drop contact area being distinguished from a surrounding area by a relief structure that prevents spreading of the liquid volume on the second surface of the body, wherein the body further comprises at least one conduit that leads into the at least one drop contact area from the direction of the first surface of the body, the conduit comprising a culture compartment that is situated close to the second surface of the body and that comprises at least a part of the drop contact area, wherein the culture compartment comprises a widened portion of the conduit, and wherein the culture compartment has a shape consisting of a first truncated cone oriented such that a larger diameter opening of the first truncated cone is arranged at the second surface of the body.

17. The set according to claim 16, wherein the hanging drop plate comprises a relief structure selected from a group that comprises a rim, a bulge, a depression, an elevation, and any combination thereof and is located in or on the second surface.

18. The set according to claim 16, wherein the conduit penetrates the entire body in essentially perpendicular direction from the first surface to the second surface.

19. The set according to claim 16, wherein the conduit partly penetrates the body in a essentially perpendicular direction in the region of the at least one drop contact area and partly extends essentially parallel to the second surface.

20. The set according to claim 16, wherein the conduit comprises an un-branched channel that essentially extends perpendicular to the first and second surfaces, wherein all portions of the conduit are coaxially aligned.

21. The set according to claim 16, wherein the conduit comprises a branched channel comprising channel parts that essentially extend perpendicular to the first and second surfaces and branch parts that essentially extend parallel to the second surface.

22. The set according to claim 16, further comprising two cover plates, one of the cover plates configured for use as a bottom plate of the hanging drop plate and the other of the cover plates configured for use as a plate for the hanging drop plate.

23. A set for cultivating cells or for producing molecular aggregates, the set comprising one hanging drop plate; wherein the hanging drop plate comprises a body with a first surface and a second surface that is essentially coplanar to the first surface and that comprises at least one drop contact area for adherently receiving a liquid volume for cultivating cells or for producing molecular aggregates therein, the at least one drop contact area being distinguished from a surrounding area by a relief structure that prevents spreading of the liquid volume on the second surface of the body, wherein the body further comprises at least one conduit that leads into the at least one drop contact area from the direction of the first surface of the body, the conduit comprising a culture compartment that is situated close to the second surface of the body and that comprises at least a part of the drop contact area, wherein the culture compartment comprises a widened portion of the conduit, wherein the culture compartment has a shape consisting of ½ of a hyperboloid, and having a shape of a divergent part of the hyperboloid.

24. The set according to claim 23, wherein the hanging drop plate comprises a relief structure selected from a group that comprises a rim, a bulge, a depression, an elevation, and any combination thereof and is located in or on the second surface.

25. The set according to claim 23, wherein the conduit penetrates the entire body in essentially perpendicular direction from the first surface to the second surface.

26. The set according to claim 23, wherein the conduit penetrates the body in an essentially perpendicular direction in the region of the at least one drop contact area and partly extends essentially parallel to the second surface.

27. The set according to claim 23, wherein the conduit comprises an un-branched channel that essentially extends perpendicularly to the first and second surfaces, wherein all portions of the conduit are coaxially aligned.

28. The set according to claim 23, wherein the conduit comprises a branched channel comprising channel parts that essentially extend perpendicularly to the first and second surfaces and branch parts that essentially extend parallel to the second surface.

29. The set according to claim 23, further comprising two cover plates, one of the cover plates configured for use as a bottom plate of the hanging drop plate and the other of the cover plates configured for use as a top for the hanging drop plate.

30. A method of cultivating cells or of producing molecular aggregates in at least one liquid volume that adheres to a drop contact area of a hanging drop plate; wherein the hanging drop plate comprises a body with a first surface and a second surface that is essentially coplanar to the first surface and that comprises at least one drop contact area for adherently receiving a liquid volume for cultivating cells or for producing molecular aggregates therein, the at least one drop contact area being distinguished from a surrounding area by a relief structure that prevents spreading of the liquid volume on the second surface of the body, wherein the body further comprises at least one conduit that mouths into the at least one drop contact area from the direction of the first surface of the body, and wherein a liquid volume is applied to a drop contact area through a conduit that leads into the drop contact area from the direction of the first surface of the body, the conduit comprising a culture compartment that is situated close to the second surface of the body and that comprises at least a part of the drop contact area, wherein the culture compartment comprises a widened portion of the conduit, and wherein the culture compartment has a shape consisting of at least one of:

a first truncated cone oriented such that a larger diameter opening of the first truncated cone is arranged at the second surface of the body; and ½ of a hyperboloid, wherein the shape comprises a divergent part of the hyperboloid.

31. The method according to claim 30, wherein a number of cells or cellular micro-aggregates of at least one cell type are suspended in a liquid, moved through a conduit of the hanging drop plate together with a liquid volume, cultivated within the liquid volume; and a microtissue is formed within the liquid volume from the cultivated cells.

32. The method according to claim 30, wherein a number of cells or cellular micro-aggregates of at least one cell type are moved through a conduit of the hanging drop plate into a liquid volume, cultivated within the liquid volume; and a microtissue is formed within the liquid volume from the cultivated cells 33. The method according to claim 30, wherein a number of molecules or molecular micro-aggregates are suspended in a liquid, moved through a conduit of the hanging drop plate together with a liquid volume from the incubated molecules or molecular micro-aggregates.

34. The method according to claim 30, wherein a part of the liquid in the liquid volume is withdrawn through the respective conduit of the hanging drop plate that is dedicated to the drop contact area.

35. The method according to claim 34, wherein at least a part of the withdrawn liquid is replaced by a liquid that is delivered through the respective conduit of the hanging drop plate that is dedicated to the drop contact area.

* * * * *